(12) United States Patent
Stensrud et al.

(10) Patent No.: US 10,023,586 B2
(45) Date of Patent: Jul. 17, 2018

(54) ENHANCED REGIO-SELECTIVITY IN GLYCOL ACYLATION

(71) Applicant: ARCHER DANIELS MIDLAND COMPANY, Decatur, IL (US)

(72) Inventors: Kenneth Stensrud, Decatur, IL (US); Erik Hagberg, Decatur, IL (US); Erin Rockafellow, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 177 days.

(21) Appl. No.: 15/102,284

(22) PCT Filed: Dec. 11, 2014

(86) PCT No.: PCT/US2014/069698
§ 371 (c)(1),
(2) Date: Jun. 7, 2016

(87) PCT Pub. No.: WO2015/094894
PCT Pub. Date: Jun. 25, 2015

(65) Prior Publication Data
US 2017/0002018 A1  Jan. 5, 2017

Related U.S. Application Data

(60) Provisional application No. 61/918,144, filed on Dec. 19, 2013.

(51) Int. Cl.
*C07D 493/00* (2006.01)
*C07D 493/04* (2006.01)

(52) U.S. Cl.
CPC ................. *C07D 493/04* (2013.01)

(58) Field of Classification Search
CPC .................................................... C07D 493/04
USPC ............................................................ 549/464
See application file for complete search history.

(56) References Cited

U.S. PATENT DOCUMENTS

2012/0171738 A1* 7/2012 Hauer ..................... C12N 9/20
435/135
2013/0123520 A1* 5/2013 Howard .................. C07C 67/00
549/464

FOREIGN PATENT DOCUMENTS

KR       20130117526       * 10/2013

OTHER PUBLICATIONS

Trahanosky et al, Isosorbide: Enantiopure alcohols Derived from Glucose, Fuel Chemistry Division Prepints, 2002, 47(1), p. 368-369 (Year: 2002).*

* cited by examiner

*Primary Examiner* — Taylor V Oh
(74) *Attorney, Agent, or Firm* — William B. Miller

(57) ABSTRACT

A method for acid-catalyzed acylation of an isohexide is described. The method involves a reaction of an isohexide and an excess of carboxylic acid in the presence of a Lewis acid or a Brnsted acid catalyst. One or more Lewis acid or Brnsted acid can facilitate conversion of isohexides to their corresponding mono and diesters with a pronounced greater regio-selectivity of exo-OH over endo-OH of the isohexide in the product. Particular catalytic acid species include zirconium chloride ($ZrCl_4$) and phosphonic acid ($H_3PO_3$), which manifest a ratio of exo:endo regioselectivity of about 5.0≠3:1 and about 4.00.3:1, respectively.

11 Claims, 5 Drawing Sheets

ENHANCED REGIO-SELECTIVITY IN GLYCOL ACYLATION

BENEFIT OF PRIORITY

The present application is a national stage entry of International Application No. PCT/US2014/069698, filed Dec. 11, 2014, which itself claims benefit of priority of U.S. Provisional Application No. 61/918,144, filed on Dec. 19, 2013, the contents of which are incorporated herein by reference.

FIELD OF INVENTION

The present disclosure relates to certain cyclic bi-functional materials that are useful as monomers in polymer synthesis, as well as intermediate chemical compounds. In particular, the present invention pertains to esters of 1,4:3,6-dianhydrohexitols and methods for their preparation.

BACKGROUND

Traditionally, polymers and commodity chemicals have been prepared from petroleum-derived feedstock. As petroleum supplies have become increasingly costly and difficult to access, interest and research has increased to develop renewable or "green" alternative materials from biologically-derived sources for chemicals that will serve as commercially acceptable alternatives to conventional, petroleum-based or -derived counterparts, or for producing the same materials as produced from fossil, non-renewable sources.

One of the most abundant kinds of biologically-derived or renewable alternative feedstock for such materials is carbohydrates. Carbohydrates, however, are generally unsuited to current high temperature industrial processes. Compared to petroleum-based, hydrophobic aliphatic or aromatic feedstocks with a low degree of functionalization, carbohydrates such as polysaccharides are complex, over-functionalized hydrophilic materials. As a consequence, researchers have sought to produce biologically-based chemicals that can be derived from carbohydrates, but which are less highly functionalized, including more stable bi-functional compounds, such as 2,5-furandicarboxylic acid (FDCA), levulinic acid, and 1,4:3,6-dianhydrohexitols.

1,4:3,6-Dianhydrohexitols (also referred to herein as isohexides) are derived from renewable resources from cereal-based polysaccharides. Isohexides embody a class of bicyclic furanodiols that derive from the corresponding reduced sugar alcohols (D-sorbitol, D-mannitol, and D-iditol respectively). Depending on the chirality, three isomers of the isohexides exist, namely: A) isosorbide, B) isomannide, and C) isoidide, respectively; the structures of which are illustrated in Scheme A.

Scheme A:

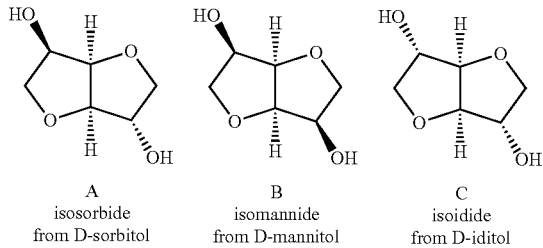

A  
isosorbide  
from D-sorbitol

B  
isomannide  
from D-mannitol

C  
isoidide  
from D-iditol

These molecular entities have received considerable interest and are recognized as valuable, organic chemical scaffolds for a variety of reasons. Some beneficial attributes include relative facility of their preparation and purification, the inherent economy of the parent feedstocks used, owing not only to their renewable biomass origins, which affords great potential as surrogates for non-renewable petrochemicals, but perhaps most significantly the intrinsic chiral bi-functionalities that permit a virtually limitless expansion of derivatives to be designed and synthesized.

The isohexides are composed of two cis-fused tetrahydrofuran rings, nearly planar and V-shaped with a 120° angle between rings. The hydroxyl groups are situated at carbons 2 and 5 and positioned on either inside or outside the V-shaped molecule. They are designated, respectively, as endo or exo. Isoidide has two exo hydroxyl groups, while the hydroxyl groups are both endo in isomannide, and one exo and one endo hydroxyl group in isosorbide. The presence of the exo substituents increases the stability of the cycle to which it is attached. Also exo and endo groups exhibit different reactivities since they are more or less accessible depending on the steric requirements of the derivatizing reaction.

As interest in chemicals derived from natural resources is increases, potential industrial applications have generated interest in the production and use of isohexides. For instance, in the field of polymeric materials, the industrial applications have included use of these diols to synthesize or modify polycondensates. Their attractive features as monomers are linked to their rigidity, chirality, iron-toxicity, and the fact that they are not derived from petroleum. For these reasons, the synthesis of high glass transition temperature polymers with good thermo-mechanical resistance and/or with special optical properties is possible. Also the innocuous character of the molecules opens the possibility of applications in packaging or medical devices. For instance, production of isosorbide at the industrial scale with a purity satisfying the requirements for polymer synthesis suggests that isosorbide can soon emerge in industrial polymer applications. (See e.g., F. Fenouillot et al., "Polymers From Renewable 1,4:3,6-Dianhydrohexitols (Isosorbide, Isommanide and Isoidide): A Review," PROGRESS IN POLYMER SCIENCE, vol. 35, pp. 578-622 (2010); or X. Feng et al., "Sugar-based Chemicals for Environmentally sustainable Applications," CONTEMPORARY SCIENCE OF POLYMERIC MATERIALS, Am. Chem. Society, December 2010; or isosorbide-based plasticizers, e.g., U.S. Pat. No. 6,395,810, contents of each are incorporated herein by reference.)

SUMMARY OF THE INVENTION

The present disclosure describes, in part, a method for the acid-catalyzed acylation of an isohexide compound. Generally, the method involves performing a Fischer esterification with an isohexide and an excess of carboxylic acid, in the presence of a Lewis acid or a Brønsted acid catalyst at a specific reaction temperature and for a time sufficient to produce a corresponding monoester product with a ratio of exo/endo regioselectivity of at least 3.4:1. The reaction is performed at a temperature from about 150° C. to about 250° C., for a period of up to about 24 hours. Typically, the reaction time is within about 10 or 12 hours, preferably between about 10-40 minutes and about 5-12 hours, typically within 6-8 hours. Typically, the reaction temperature ranges from about 170° C. to 220° C., preferably from about 175° C. to about 205° C.

In the present method, the isohexide is at least one or more of the following: isosorbide, isomannide, and isoidide. The carboxylic acid can be at least an alkanoic, alkenoic, alkyonoic, and aromatic acid, having a carbon chain length ranging from $C_2$-$C_{26}$. In certain embodiments, the cabozylica acid can be 2-ethylhexanoic acid, hexanoic acid, or octanoic acid.

The carboxylic acid is present in about 2-fold to about 10-fold molar excess relative to the isohexide content, typically about 3-fold molar excess.

The Lewis acid is at least: tin (II)-2-ethylhexanoate, dibutyl-tin (II) chloride, hafnium choride, dibutyl-tin maleate, tin (II) chloride, titanium (IV) chloride, bismuth chloride, lanthanum (III) triflate, dibutyl-tin (IV) oxide, iron (III) triflate, aluminum chloride, bismuth triflate, gallium triflate, scandium triflate, or a combination thereof. Desirably, the Lewis acid is zirconium (IV) chloride. The Brønsted acid is: sulfuric acid, or p-toluenesulfonic acid, or phosphonic acid. The ratio of the exo/endo regioselectivity ranges from about 3.4:1 to about 3.9:1 or for the Lewis acid and Brønsted acid catalysts. The ratio of the exo/endo regioselectivity is about 3.8:1 to about 4.4:1 when phosphonic acid is the Brønsted acid catalyst. The ratio of the exo/endo regioselectivity is about 4.9:1 to about 5.3:1 when zirconium (IV) chloride is the Lewis acid catalyst.

The Lewis acid is present in an amount of catalyst loading that ranges from about 0.0001 wt. % to about 10 wt. %. The Lewis acid and Brønsted acid are each present in an amount of catalyst loading that is from about 3 wt % to about 8 wt. %.

In another aspect, the present disclosure also pertains to a monoester product formed from a reaction of an isohexide and an acid, using either a Lewis acid or Brønsted acid catalyst at a temperature in a range from about 150° C. to about 250° C., and exhibiting a preference of exo over endo regioselectivity.

DETAILED DESCRIPTION OF THE INVENTION

Section I.—Description

Figure 1:
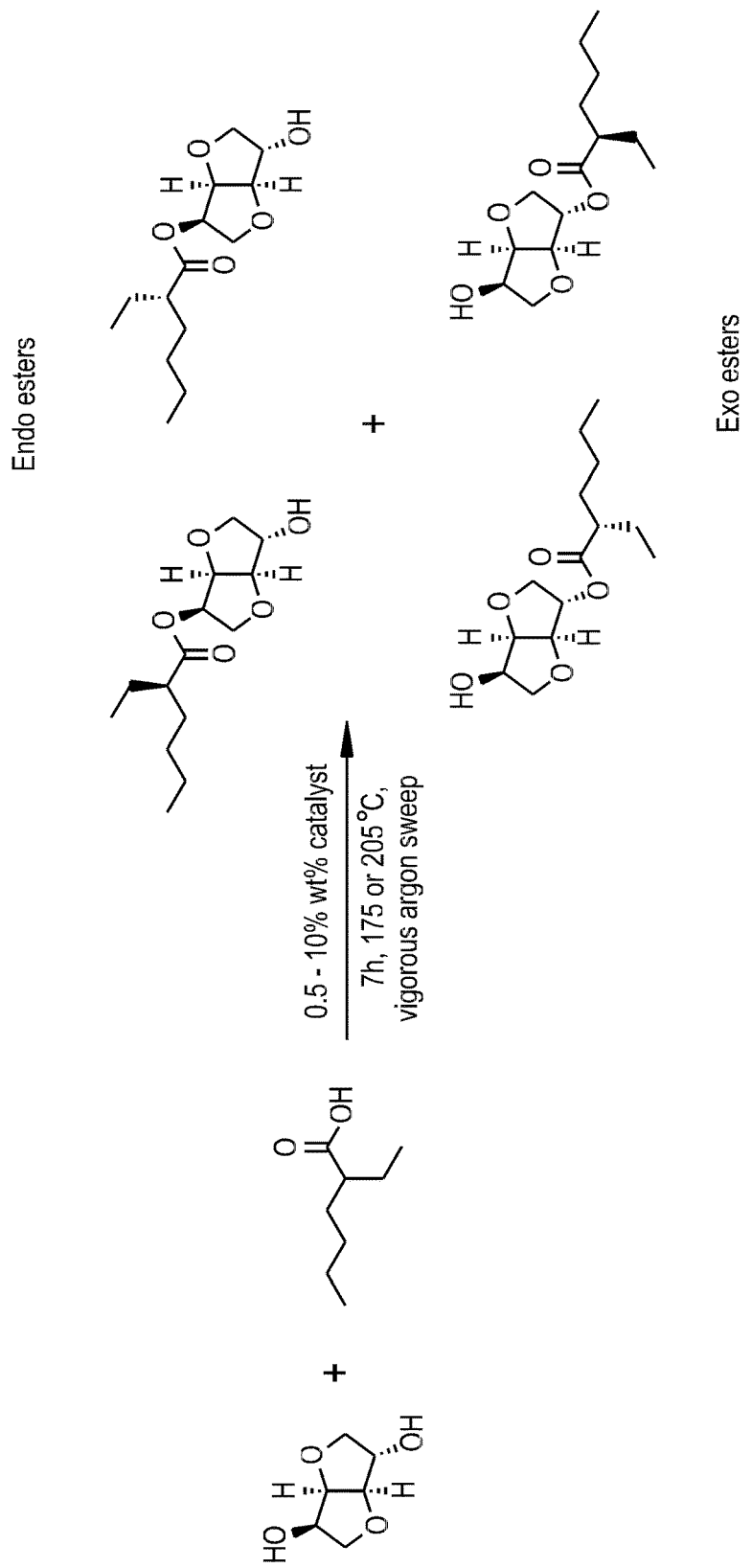
FIG. 1, is a schematic representation of the overall synthesis of monoesters, exo and endo product.

As biomass derived compounds that afford great potential as surrogates for non-renewable petrochemicals, 1,4:3,6-dianhydrohexitols are a class of bicyclic furanodiols that are valued as renewable molecular entities. (For sake of convenience, 1,4:3,6-dianhydrohexitols will be referred to as "isohexides" in the Description hereinafter.) As referred to above, the isohexides are good chemical platforms that have recently received interest because of their intrinsic chiral bi-functionalities, which can permit a significant expansion of both existing and new derivative compounds that can be synthesized.

Isohexide starting materials can be obtained by known methods of making respectively isosorbide, isomannide, or isoidide. Isosorbide and isomannide can be derived from the dehydration of the corresponding sugar alcohols, D-sorbitol and D mannitol. As a commercial product, isosorbide is also available easily from a manufacturer. The third isomer, isoidide, can be produced from L-idose, which rarely exists in nature and cannot be extracted from vegetal biomass. For this reason, researchers have been actively exploring different synthesis methodologies for isoidide. For example, the isoidide starting material can be prepared by epimerization from isosorbide. In L. W. Wright, J. D. Brandner, *J. Org. Chem.*, 1964, 29 (10), pp. 2979-2982, epimerization is induced by means of Ni catalysis, using nickel supported on diatomaceous earth. The reaction is conducted under relatively severe conditions, such as a temperature of 220° C. to 240° C. at a pressure of 150 atmosphere. The reaction reaches a steady state after about two hours, with an equilibrium mixture containing isoidide (57-60%), isosorbide (30-36%) and isomannide (5-7-8%). Comparable results were obtained when starting from isoidide or isomannide. Increasing the pH to 10-11 was found to have an accelerating effect, as well as increasing the temperature and nickel catalyst concentration. A similar disclosure can be found in U.S. Pat. No. 3,023,223, which proposes to isomerize isosorbide or isomannide. More recently, P. Fuertes proposed a method for obtaining L-iditol (precursor for isoidide), by chromatographic fractionation of mixtures of L-iditol and L-sorbose (U.S. Patent Publication No. 2006/0096588; U.S. Pat. No. 7,674,381 B2). L-iditol is prepared starting from sorbitol. In a first step sorbitol is converted by fermentation into L-sorbose, which is subsequently hydrogenated into a mixture of D-sorbitol and L-iditol. This mixture is then converted into a mixture of L-iditol and L-sorbose. After separation from the L-sorbose, the L-iditol can be converted into isoidide. Thus, sorbitol is converted into isoidide in a four-step reaction, in a yield of about 50%. (The contents of the cited references are incorporated herein by reference.)

We have found that one or more Lewis acid and/or Brønsted acid can facilitate conversion of isohexides to their corresponding mono and diesters with a pronounced greater regio-selectivity of exo-OH over endo-OH of the isohexide in the product. Particular catalytic acid species include, for example, zirconium chloride ($ZrCl_4$), a Lewis acid, and phosphonic acid ($H_3PO_3$), a reducing Brønsted acid (also known as phosphorus acid), which manifest a ratio of exo:endo regioselectivity of about 5.0±0.3:1 and about 4.0±0.3:1, respectively.

Phosphonic acid, which is a crystalline solid, commercially available, inexpensive, and possesses a strong acidity (pKa ~1). This material evinces both high catalytic activity in the context of Fischer esterifications and pronounced color attenuation of the product mixture. To date, we believe that phosphonic acid has not received significant attention in this regard, either as a Brønsted acid in the catalysis of isohexide acetylation with carboxylic acids, concerning color mitigation of products or concerning high isohexide conversions. Further, at this time, phosphonic acid is one that manifests both high reactivity and concomitant color diminution.

FIG. 1 shows a general schematic representation of the reaction to prepare isosorbide monoesters, which form enantiomer pairs of exo and endo species.

For the acid catalysts, according to embodiments of the present reaction, the ratio of exo/endo regioselectivity is at least 3.40:1 or 3.45:1. Table 1 summarizes the relative regioselectivity of the exo/endo-hydroxyl groups in the synthesis of isohexide monoesters using examples of different kinds of acid catalysts. Table 1 lists and compares the efficacy of the different acid catalyst species in terms of their product color, catalyst load, and conversion rate relative to $ZrCl_4$. The zirconium (IV) chloride, a preferred Lewis acid embodiment, displays a significantly augmented regioselectivity of about 4.9:1 to about 5.3:1 exo/endo monoesters (e.g., 5:0:1 to about 5:2:1) relative to other acid catalyst species. Most of the other acid catalysts exhibit ~3.4:1 or 3.5:1 exo/endo regioselectivity and relatively low rates of conversion, irrespective of catalyst load. Some other catalysts have an exo/endo ratio of about 3.6:1 to about 3.8:1. Also, the zirconium (IV) chloride (~5:1) exo/endo ratio is about two times greater than the ratio of the strong acid catalysts. The strong acid catalysts (i.e., sulfuric acid, p-toluenesulfonic acid) exhibited higher rates of conversion, but an even lower exo/endo ratio, respectively, 2.03:1 or 2.26:1. As a baseline, autocatalysis without using an acid catalyst results in about 3.40:1 ratio of exo/endo regioselectivity, with minimal conversion of the isohexide to its corresponding ester product.

Figure 2:
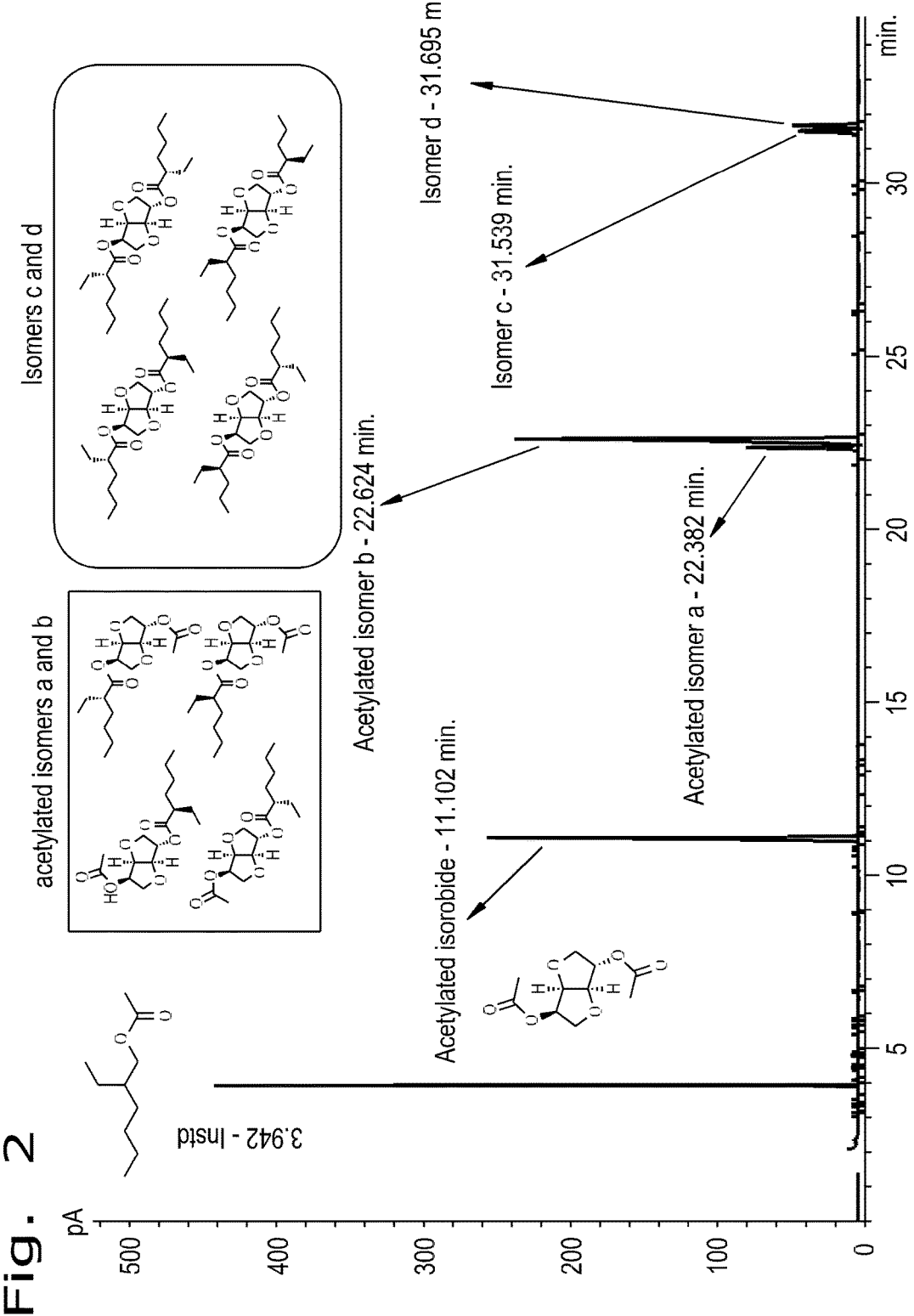
FIG. 2, shows a chromatogram of results obtained from quantitative analysis conducted by gas chromatography (GC) of isomers synthesized according to an embodiment of the present invention.

FIG. 2, is a representative chromatogram of the results obtained from quantitative analysis conducted by gas chromatography (GC) of the two sets of four isomers synthesized according to the reaction above.

Figure 3:
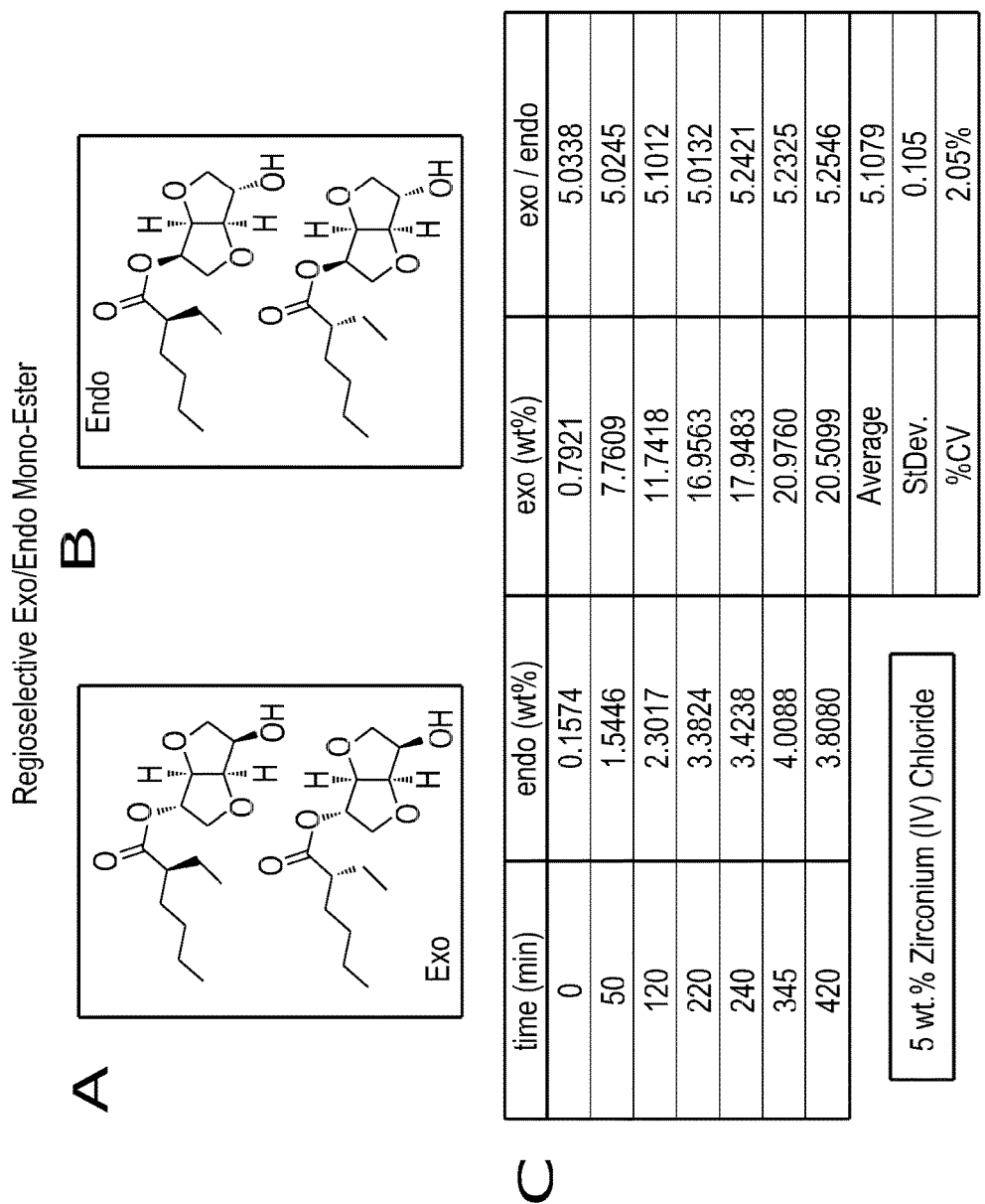
FIG. 3, shows pairs of enantiomer and a table summarizing the regioselectivity of exo/endo preference in converting to monoesters that are produced with $ZrCl_4$ as the catalyst.

FIG. 3, presents enantiomer pairs, assigned exo (A) and endo (B), of isohexide monoesters. Accompanying Table (C) presents the GC analysis of aliquots sampled over a reaction period of about 420 minutes. The reaction uses a Lewis acid, zirconium (IV) chloride, at 5 wt. % relative to the isohexide content. The results suggest that isoidide, having only exo-OH groups, is most reactive, and isomannide, having only endo-OH groups, is least reactive. The result for isosorbide, having both an exo-OH and an endo-OH, is expected to be in the middle.

Figure 4:
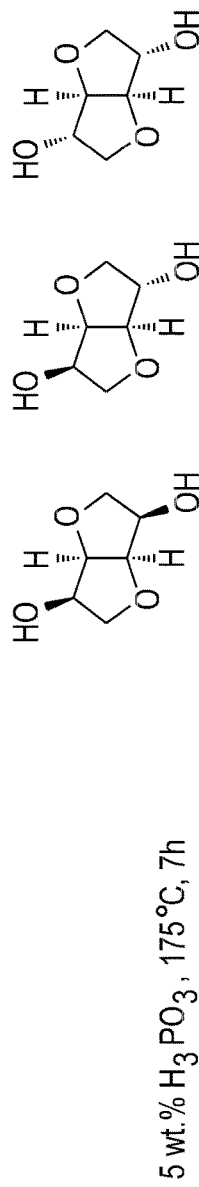
FIG. 4, is a graph that compares the relative regioselective preference of endo/exo-hydroxyl groups in terms of the percentage rate that each of the three isohexide species (isomannide, isosorbide, and isoidide) are converted to their corresponding esters with phosphonic acid as the catalyst.
Figure 4:
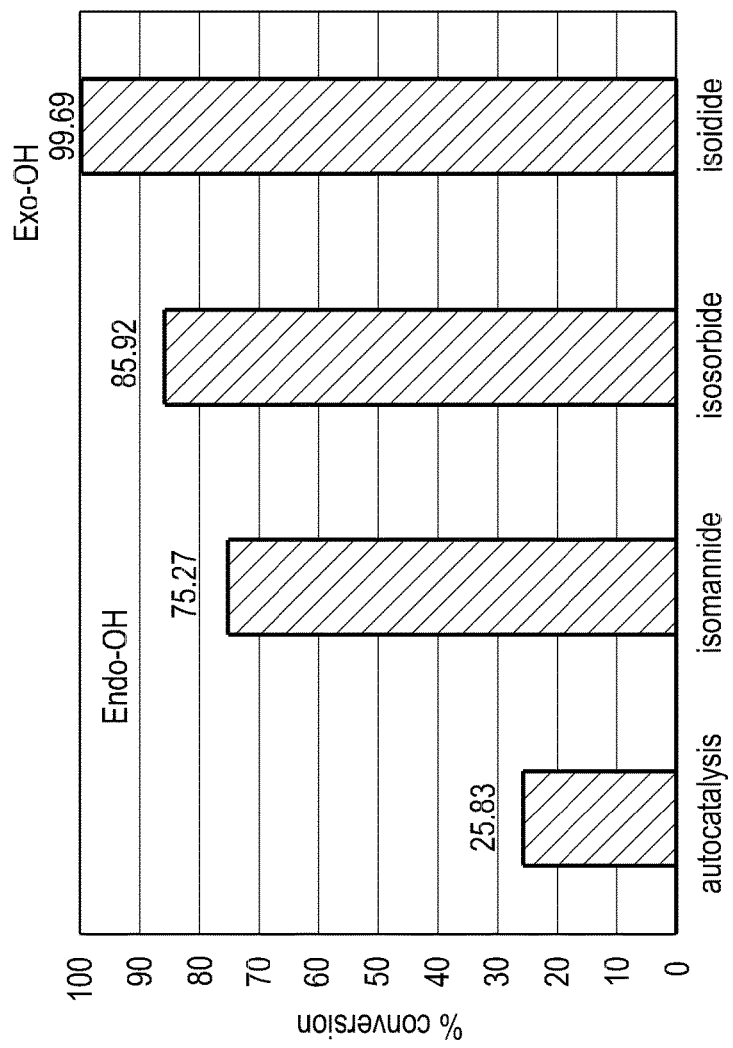

Similarly, FIG. 4, summaries the results from an embodiment using a Brønsted acid catalyst. The reaction is performed using about 5 wt. % phosphonic acid ($H_3PO_3$) at 175° C. for 7 hours. The percent conversion, relative to endo-OH vs. exo-OH, for the three isohexide compound species. Isomannide having only endo-hydroxyl groups showed the lowest conversion at about 75.27%, while isoidide having only exo-hydroxyl groups showed almost complete conversion at about 99.69%. Isosorbide, having both an exo and endo-hydroxyl group is in between at about 86.92% conversion. Phosphonic acid appears to contribute to a preferential regioselectivity of exo over endo of about 3.8:1 to about 4.4:1, (e.g., 4.1:1, 4.2:1, or 4.3:1).

Table 2, lists the results of acylation reactions using 2-ethyl-hexanoic (2EH) acid esterification with isosorbide at 175° C., 7 h. Again, the results suggest that phosphonic acid exhibits greater regioselectivity for the exo-OH over the endo-OH of an isohexide molecule in a ratio of about 4:1. Phosphonic acid catalyzes effectively the esterification with 2EH for significant (e.g., ~90%-100%) isosorbide conversion, for instance, at 205° C., 5 h.

TABLE 1

Monoester Regioselectivity

| Catalyst | Loading (wt. % vs. isosorbide) | Exo/Endo | Std. Dev. | % Conversion | Δ Exo/Endo (relative to Autocatalysis) |
|---|---|---|---|---|---|
| Autocatalysis | 0.0 | 3.40 | 0.03 | 0.87 | 0 |
| Sn(II)-2EH | 5.1 | 3.59 | 0.10 | 2.89 | 0.15 |
| (butyl)$_2$SnCl$_2$ | 5.2 | 3.68 | 0.04 | 1.04 | 0.24 |
| HaCl$_4$ | 5.4 | 3.51 | 0.07 | 2.12 | 0.06 |
| (butyl)$_2$Sn(laurate)$_2$ | 5.1 | 3.68 | 0.11 | 2.86 | 0.23 |
| ZrCl$_4$ | 5.4 | 5.02 | 0.07 | 1.38 | 1.57 |
| ZrCl$_4$ | 5.7 | 5.15 | 0.04 | 0.88 | 1.71 |
| (butyl)$_2$Sn(maleate) | 5.3 | 3.77 | 0.10 | 2.60 | 0.32 |
| SnCl$_4$ | 5.7 | 2.42 | 0.73 | 30.17 | −1.03 |
| SnCl$_2$ | 5.7 | 3.40 | 0.09 | 2.66 | −0.06 |
| BiCl$_3$ | 5.7 | 3.52 | 0.05 | 1.40 | 0.08 |
| Dibutyltin(IV)oxide | 5.7 | 3.75 | 0.09 | 2.41 | 0.31 |
| Sulfuric acid | 1.0 | 2.03 | 0.53 | 26.10 | −1.42 |
| p-Toluenesulfonic acid | 1.0 | 2.26 | 0.55 | 24.38 | −1.19 |

Figure 5:
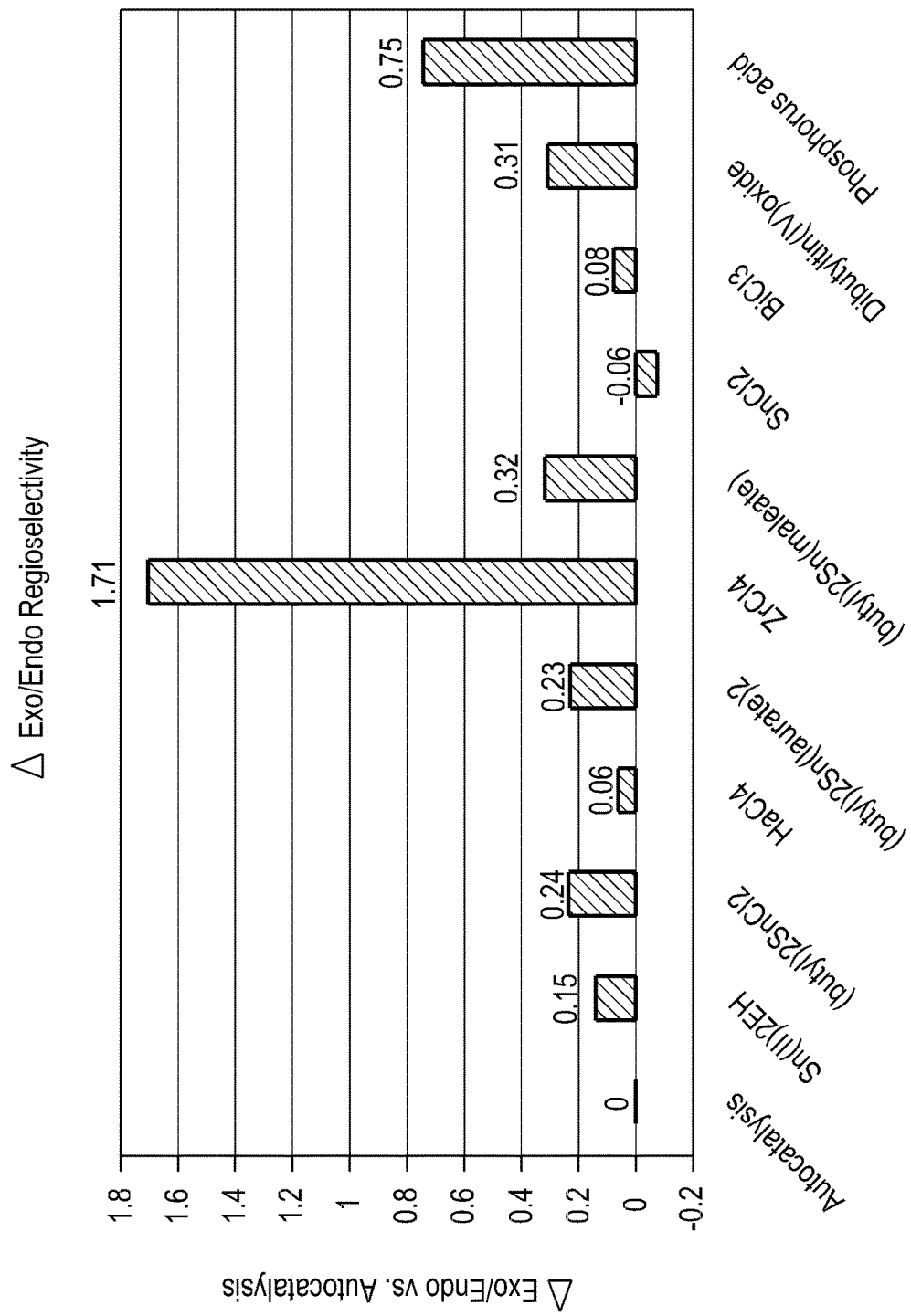
FIG. 5, is a graph that shows the relative change in regioselectivity of isohexide compounds as compared to an autocatalysis baseline. The change in regioselectivity for $ZrCl_4$ and phosphonic acid is pronounced relative to other catalysts.

The ZrCl$_4$ samples exhibit a change (Δ) in exo/endo ratio relative to autocatalysis of 1.5 to about 1.71. These results appear to be significantly higher—about at least 1.2 units greater—than the change exhibited by the other catalyst species, which either are no greater than about 0.2 or 0.3, or have a negative value. This degree of change suggests that the ZrCl$_4$ catalyst manifests a greater regioselectivity for exo-hydroxyl groups over endo-hydroxyl groups. These results are presented in FIG. 5, which illustrates graphically the effective regioselectivity of ZrCl$_4$ over the other catalyst species. Phosphonic acid catalyst also shows an improved change in exo/endo ratio of about 0.75 relative to the baseline.

TABLE 2

$H_3PO_3$ Catalysis Results: 2-Ethyl-Hexanoic Acid Esterification with Isosorbide, 175° C., 7 h.

| Sample | Loading (wt. % vs. isosorbide) | APHA (color) | % Isosorbide conversion | Exo/Endo (mean) | Exo/Endo (std. dev.) | % Conversion |
|---|---|---|---|---|---|---|
| 1. Comp. | 0 | 96 | | | | |
| 2. | 11.6 | 137 | 93.99 | 4.05 | 0.07 | 1.59 |
| 3. | 6.7 | 145 | 87.73 | 3.95 | 0.08 | 2.02 |
| 4. | 4.9 | 151 | 85.92 | 4.09 | 0.08 | 2.02 |
| 5. | 3.6 | 168 | 58.79 | 4.02 | 0.10 | 2.37 |
| 6. | 1.3 | 181 | 44.92 | 3.96 | 0.08 | 2.00 |

N.B.: Product mixture from samples of catalysts typically used manifest APHA >275.

Additionally, the phosphonic acid manifests antioxidant properties, and can greatly reduce color body development relative to the other acid catalysts described herein. A reaction using 5 wt. % $H_3PO_3$, 205° C., 7 h, generates a reaction product mixture having color with APHA value=98. A baseline color for distilled 2EH is APHA value=6. The APHA color scale, also referred to as the Hazen scale, is a color standard named for the American Public Health Association and defined by ASTM D1209. The scale for APHA color goes from 0 to 500 in units of parts per million of platinum cobalt to water. Zero on this scale represents distilled water, or what is more commonly called white water.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. A method for acid-catalyzed acylation of isosorbide, comprising contacting isosorbide with an excess of carboxylic acid in the presence of a Lewis acid catalyst at a reaction temperature and for a time sufficient to produce a corresponding monoester product with a ratio of exo/endo regioselectivity of at least 3.4:1, wherein said Lewis acid catalyst is selected from the group consisting of tin (II)-2-ethylhexanoate, dibutyl-tin (II) chloride, tin (II) chloride, hafnium chloride, dibutyl-tin maleate, titanium (IV) chloride, zirconium (IV) chloride, bismuth chloride, lanthanum (III) triflate, dibutyl-tin (IV) oxide, iron (III) triflate, aluminum chloride, bismuth triflate, gallium triflate, scandium triflate, and combinations of these.

2. The method according to claim 1, wherein said reaction temperature is from 150° C. to 250° C.

3. The method according to claim 1, wherein said reaction temperature is from 170° C. to 220° C.

4. The method according to claim 1, wherein said reaction time is less than 24 hours.

5. The method according to claim 4, wherein said reaction time is 5-12 hours.

6. The method according to claim 1, wherein said carboxylic acid is selected from an alkanoic, alkenoic, alkyonoic, and aromatic acid, having a carbon chain length ranging from $C_2$-$C_{26}$.

7. The method according to claim 1, wherein said carboxylic acid is present in 2-fold to 10-fold molar excess relative to the isosorbide.

8. The method according to claim 7, wherein said carboxylic acid is present in 3-fold molar excess relative to the isosorbide.

9. The method according to claim 1, wherein the ratio of said exo/endo regioselectivity ranges from about 3.5:1 to about 3.9:1.

10. The method according to claim 1, wherein said Lewis acid is zirconium (IV) chloride.

11. The method according to claim 1, wherein said Lewis acid is present in an amount of catalyst loading that ranges from 0.0001 wt. % to 10 wt. % relative to the isosorbide content.

* * * * *